United States Patent
Faber et al.

(10) Patent No.: US 7,561,910 B2
(45) Date of Patent: Jul. 14, 2009

(54) METHOD FOR DETERMINATION OF THE SUPPORTED POSITION OF A PATIENT IN A MAGNETIC RESONANCE APPARATUS

(75) Inventors: Roland Faber, Uttenreuth (DE); Oliver Schreck, Shen Zen (CN)

(73) Assignee: Siemens Aktiengesellschaft, Munich (DE)

( * ) Notice: Subject to any disclaimer, the term of this patent is extended or adjusted under 35 U.S.C. 154(b) by 112 days.

(21) Appl. No.: 11/408,686

(22) Filed: Apr. 20, 2006

(65) Prior Publication Data

US 2006/0264737 A1      Nov. 23, 2006

(30) Foreign Application Priority Data

Apr. 20, 2005   (DE) ................. 10 2005 018 349

(51) Int. Cl.
    *A61B 5/05* (2006.01)
(52) U.S. Cl. ........................... 600/410; 324/307
(58) Field of Classification Search ............... 600/410, 600/411, 414, 415, 418, 421, 424
    See application file for complete search history.

(56) References Cited

U.S. PATENT DOCUMENTS

| | | | | |
|---|---|---|---|---|
| 5,810,729 A | * | 9/1998 | Hushek et al. | 600/410 |
| 6,038,466 A | * | 3/2000 | Haselhoff | 600/410 |
| 6,195,409 B1 | | 2/2001 | Chang et al. | |
| 6,325,540 B1 | * | 12/2001 | Lounsberry et al. | 378/207 |
| 6,529,762 B1 | | 3/2003 | Ladebeck | |
| 6,806,707 B2 | * | 10/2004 | Schreck | 324/307 |
| 2002/0107442 A1 | * | 8/2002 | Schreck | 600/411 |
| 2002/0198447 A1 | | 12/2002 | Van Muiswinkel et al. | |
| 2003/0098688 A1 | * | 5/2003 | Brinker et al. | 324/309 |
| 2003/0179917 A1 | * | 9/2003 | Faber et al. | 382/130 |
| 2005/0018893 A1 | * | 1/2005 | Wang et al. | 382/132 |
| 2005/0088177 A1 | * | 4/2005 | Schreck et al. | 324/307 |
| 2006/0098887 A1 | * | 5/2006 | El-Bakry et al. | 382/254 |
| 2006/0264737 A1 | * | 11/2006 | Faber et al. | 600/410 |
| 2007/0038070 A1 | * | 2/2007 | Tank | 600/410 |

FOREIGN PATENT DOCUMENTS

| | | | |
|---|---|---|---|
| DE | 10346410 | * | 5/2005 |
| WO | WO 2005/030330 | | 4/2005 |
| WO | WO 2005/033726 | | 4/2005 |

\* cited by examiner

*Primary Examiner*—Long V Le
*Assistant Examiner*—Saurel J Selkin
(74) *Attorney, Agent, or Firm*—Schiff Hardin LLP

(57) ABSTRACT

In a method and magnetic resonance apparatus for determination of the position of the apparatus scanner, three localizer exposures situated orthogonally to one another are obtained during or after the insertion of the patient into the scanner. Using these three localizer exposures, an image analyzer automatically determines anatomical markers shown in the localizer exposures, which anatomical markers are dependent on the patient position in the scanner terms of their position in the localizer exposure. The spatial position of the patient is automatically determined by the image analyzer using the markers.

9 Claims, 2 Drawing Sheets

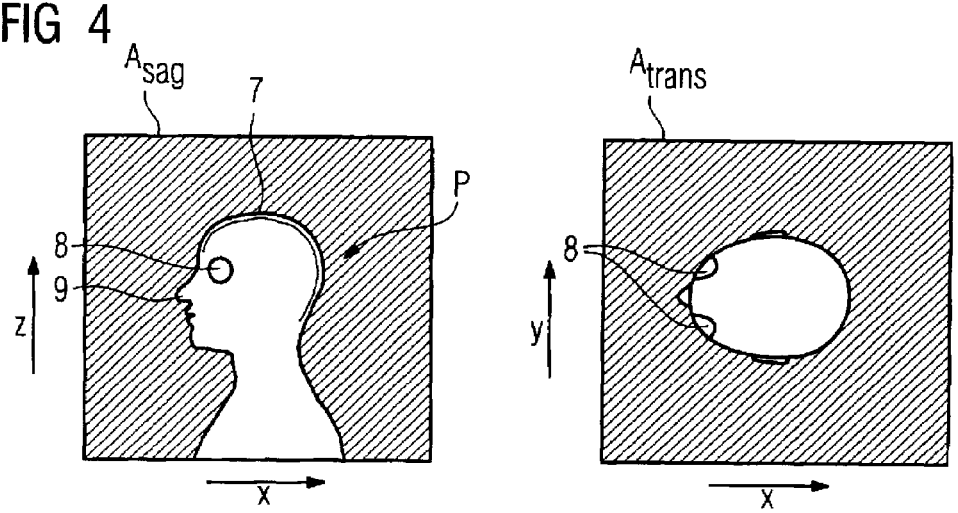
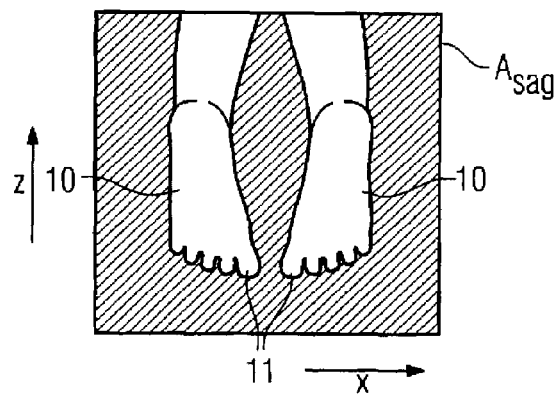
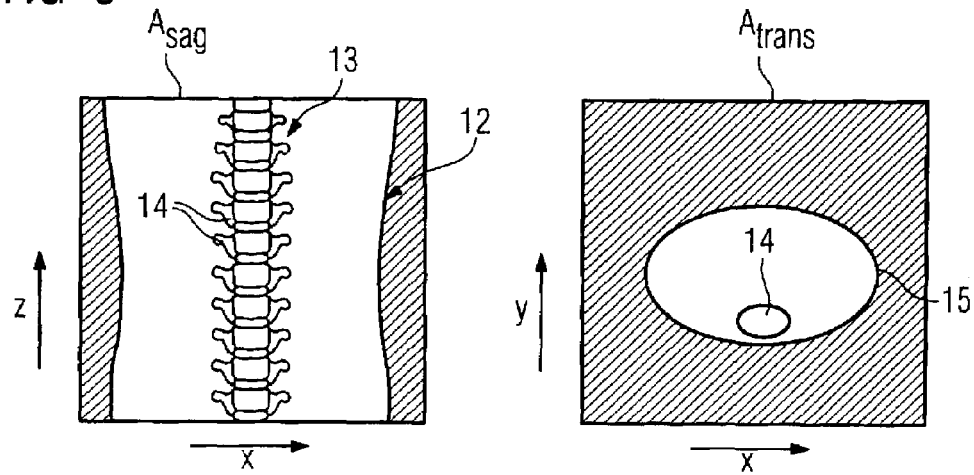

METHOD FOR DETERMINATION OF THE SUPPORTED POSITION OF A PATIENT IN A MAGNETIC RESONANCE APPARATUS

BACKGROUND OF THE INVENTION

1. Field of the Invention

The invention concerns a method for determination of the supported position of a patient in a magnetic resonance apparatus, as well as a magnetic resonance apparatus operating according to the method.

2. Description of the Prior Art

In the examination of a patient in a magnetic resonance apparatus, the patient can be supported in eight different positions. The patient can be positioned head-first or the feet-first, lying on his or her back or his or her stomach, or lying on the left side or on the right side. The detection of how the patient is currently positioned, consequently how the patient is thus arranged with regard to the coordinate system of the magnetic resonance apparatus conventionally ensues by an operating person that inputs the patient positioning into the apparatus computer at the beginning of the registration procedure. The input of the (expected or intended) patient position typically ensues before the actual positioning of the patient. If the patient positioning does not coincide with the manual input in the registration procedure, this can lead, for example, to a right-left inversion of the resulting image. This means that the identification of right and left in the acquired images does not correspond to the actual position of the patient in the magnetic resonance apparatus. This can lead to severe consequences in later operations; for example, as has actually occurred, the right kidney being operated on instead of the left. The subsequent correction of an incorrectly-entered patient position is complicated. Precise and correct detection of the patient positioning thus has a large importance, but the conventional procedure is error-prone.

SUMMARY OF THE INVENTION

An object of the present invention is to provide a method and a magnetic resonance apparatus that allow an exact detection of the supported position of a patient in the apparatus, so as to help to prevent the aforementioned problems.

This object is achieved in accordance with the invention by a method wherein three localizer exposures situated orthogonally to one another are made during or after the insertion of the patient in the apparatus, and an image analyzer, using the three localizer exposures, automatically determines one or more anatomical markers shown in the localizer exposures, the anatomical marker being dependent on the patient support in terms of its position in the localizer exposure, and automatically determines the spatial position of the patient using the marker or markers.

The inventive method accomplishes an automatic patient positioning determination that requires only three localizer exposures, that are always made beforehand anyway in the framework of an examination. These localizer exposures do not have to exhibit a high image quality since they do not serve the goal of detecting anatomical subtleties, but rather merely serve to allow rough anatomical markers or structures to be identified that are dependent on the actual patient support in terms of their position in the respective localizer exposure.

After acquisition of these fast localizer images, using the coronal, sagittal and transversal localizer slices the image analyzer determines distinctive anatomical structures that are shown in the respective images and that are unambiguous with regard to the actual patient support in terms of their image position, and that consequently give an unambiguous indication of the actual patient position. For example, if the sagittal slice shows the typical head shape or calvarium, it is thus clear that the patient was inserted head-first. Using the sagittal image, it can be determined whether the patient is situated on his or her back, his or her chest or on a side. For example, if the patient lies on his or her side, analysis of the coronal image allows identification of the orientation (supine/prone) by, for example, using the position of the nose or of the eye sockets that are situated to the right or left depending on the orientation. If the patient is lying on his or her right or left side, an analysis of the transversal image is used in order to determine the orientation (left/right), for example again using the position of the nose or of the eye sockets.

Using this automatic image analysis and determination of the anatomical markers dependent on the actual position of the patient in terms of their image position, the actual spatial support of the patient thus can be automatically determined in a fast and simple manner. This automatic determination can be the basis for the entry of the patient positioning in the already-occurred registration; alternatively, this information can serve as a control for the manual input, meaning that in this regard the medical-technical assistant has the possibility to verify his or her own input before the actual image acquisition.

For the evaluation of the localizer exposures, it is appropriate and sufficient for the image analyzer to "binarize" the localizer exposures without any gray shades, meaning that these are used as purely black-and-white representations that allow only rough outlines (contours) to be detected. Depending on which anatomical markers are sought, the binarization can ensue using fixed predetermined or grey scale value windowing parameters or grey scale value windowing parameters that can be set on the part of the user. Anatomical structures frequently differ in terms of the respective grey scale value. Depending on how the image analyzer "searches", it is possible to effect the binarization in a different manner in order to make the possibly present structure also unambiguously recognizable in the context of the image contrast. The image analysis itself appropriately ensues by corresponding analysis algorithms that enable edge detection, contour tracking etc.

As already described, it is advantageous for the automatically-determined patient position to be subsequently automatically associated with the examination images to be acquired, such that it is assured that the correct patient position is also actually associated with the respective image that, for example, is used for a later operation planning. The determined patient position can also be displayed on a monitor, connected with an input or acknowledgement request to the operating personnel who must first acknowledge the automatically-determined patient position via a suitable input before this is automatically entered into the registration or associated with the examination images that are acquired later.

In addition to the method, the invention also concerns a magnetic resonance apparatus having a control device with an image analyzer, the apparatus scanner acquiring three localizer exposures situated orthogonally to one another and during or after the insertion of the patient into the scanner. An image analyzer automatically detects one or more anatomical markers in the localizer exposures, which anatomical markers are dependent on the patient support in the scanner in terms of their position in the localizer exposure, and the spatial position of the patient in the scanner can be determined using the marker or markers.

DESCRIPTION OF THE DRAWINGS

FIG. 4 illustrates a second example of a patient positioning determination in accordance with the invention using two localizer exposures, FIG. 5 illustrates a third example of a patient positioning determination in accordance with the invention using one localizer exposure, FIG. 6 illustrates a fourth example of a patient positioning determination in accordance with the invention using two localizer exposures.

DESCRIPTION OF THE PREFERRED EMBODIMENTS

Figure 1:
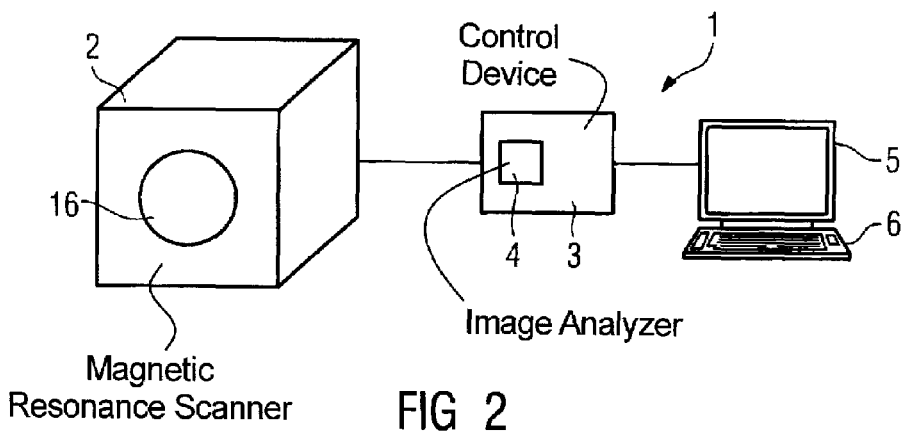
FIG. 1 is a schematic illustration of the basic components of an inventive magnetic resonance apparatus.

FIG. 1 shows an inventive magnetic resonance apparatus 1, having a magnetic resonance scanner 2 as well as an associated control device 3 which, in the shown example, includes an image analyzer 4. A monitor 5 for output of acquired images as well as an input unit 6 in the form of a keyboard are provided.

In known magnetic resonance apparatuses, the patient is typically arranged on a patient bed and inserted into the tube 16 of the scanner device 2 with a horizontal alignment of the patient bed. The shown example is a closed magnetic resonance device 2; but open devices are also known in which two device halves are arranged one atop the other and separated from one another, such that the patient can also be inserted from the side.

Figure 2:
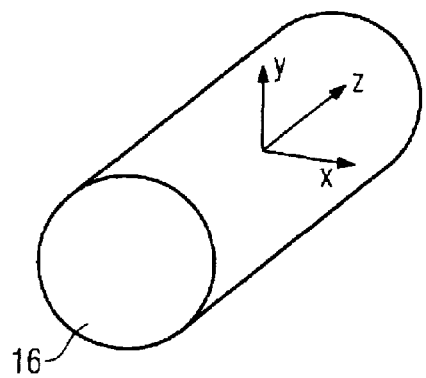
FIG. 2 shows the spatial alignment of the coronally-, sagittally- and transversally-acquired localizer exposures in accordance with the invention.

FIG. 2 shows the tube 16 as well as a coordinate system of the magnetic resonance scanner 2 using which the fixed (with regard to this device coordinate system) alignment of the coronal, sagittal and transversal localizer images is explained.

A sagittal image is acquired in the x-z plane. A coronal image is acquired in the y-z plane. A transversal image is acquired in the x-y plane. For the inventive method, the localizer exposures are thus related to the device coordinate system, but not to the patient coordinate system inherent to the body. This means that a sagittal localizer exposure does not run sagittally with regard to the patient, but rather sagittally with regard to the magnetic resonance scanner 2; the same applies for the transversal exposure and the coronal exposure.

Figure 3:
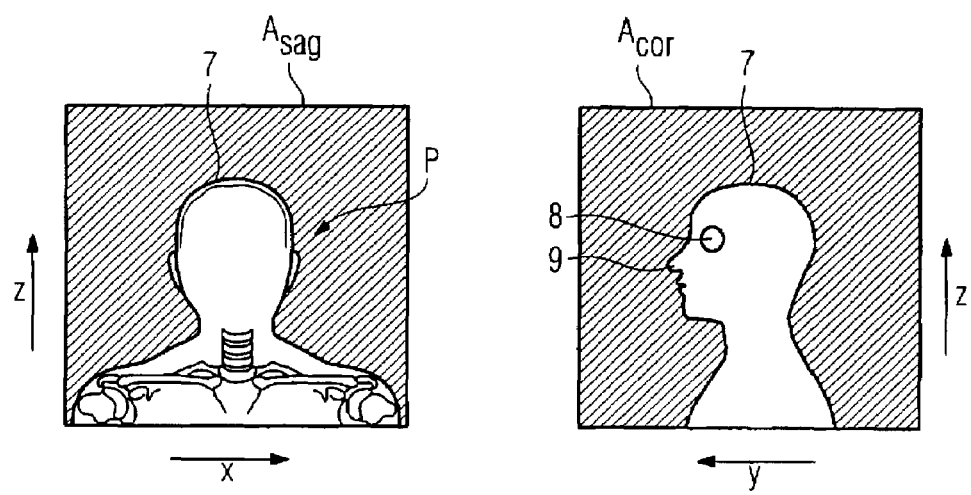
FIG. 3 illustrates a first exemplary embodiment of the patient positioning determination in accordance with the invention using two localizer exposures.

FIG. 3 shows the determination of the patient position using two localizer exposures, namely a sagittal exposure $A_{sag}$ and a coronal exposure $A_{cor}$. The respective orientations of the images in the coordinate system are specified with regard to the exposures in the coordinate system according to FIG. 2.

The individual localizer exposures (and this applies in general for all exemplary embodiments) are initially binarized by the image analyzer means 4 and consequently are processed as reduced black-and-white representations, which is sufficient in view of the fact that distinguished anatomical structures or markers are sought by the image analyzer 4 strictly for position determination. The image analyzer 4 executes suitable analysis or detection algorithms, such as edge detection algorithms etc. The binarization can ensue either using fixed, predetermined grey scale value windowings or using grey scale value windowings that can be adjusted by the user (for example, defined via the keyboard 6), in particular dependent on specific structures sought by the image analyzer 4. For a continuous automation, however, it is advantageous when fixed, predetermined grey scale value windowings form the basis of the binarization. As noted various windowings can be associated with a localizer exposure in order to be able to specifically emphasize different anatomical markers that show various grey scale values in the non-binarized image, which emphasis occurs in order to thus support the analysis.

In FIG. 3, the sagittal exposure $A_{sag}$ shows the outline (contour) 7 of the patient P. As is shown by the hatching of the bordering image region, this region is black while the patient is essentially shown in white except for a few structures that are shown black due to the associated grey scale value windowing in the framework of the binarization.

From the orientation of the head or of the head outline as well as from the circumstance that the head is even shown in the sagittal section, it is unambiguous that the patient (with regard to the z-direction) was inserted into the examination device 2 head-first. It should be noted that the localizer exposures can already have been acquired during the insertion, or after the final positioning of the patient.

In order to now determine whether the patient is lying on his or her chest or his or her back, the coronal section is analyzed by the image analyzer 4. In this black-and-white image (likewise binarized), the head outline 7 is shown again, but in a different representation as a consequence of the orthogonal positioning of the coronal section relative to the sagittal section. The image analyzer 4 now analyzes the binarized representation with regard to noticeable (conspicuous) anatomical markers such as, for example, the eye socket 8 or the position of the nose 9. Since they are arranged asymmetrically on the body, these are unambiguous to the back position of the patient P. This means that, using the simple analysis of the binarized localizer exposures, the patient position in the device coordinate system is automatically determined via the control device 3, or the image analyzer 4 thereof. This information can now be output on the monitor 5, connected with an input request to an operating personnel to acknowledge this automatically-determined position information. As described, this can ensue via the keyboard 6. As soon as the acknowledgement is present, the positioning information is, for example, automatically associated with all images subsequently acquired with the magnetic resonance device.

FIG. 4 shows two further localizer exposures in already-binarized form, namely on the one hand again a sagittal exposure $A_{sag}$ as well as a transversal exposure $A_{trans}$. The image analyzer 4 here initially evaluates the sagittal exposure $A_{sag}$ with regard to possible anatomical markers. Here the circumference 7 of the head of the patient is also shown; for example, here the calvarium is also visibly indicated. The image analyzer 4 now detects, for example, the outline 7 or, for example, the calvarium as an unambiguous anatomical marker that describes the head. This means that the patient was inserted head-first (this was already verified). In principle, using the asymmetry or, respectively, deformity of the head it has already been analyzed from the sagittal exposure shown here whether the head is directed to the right or left; further anatomical markers thus do not necessarily have to be determined in this exposure or a further exposure does not necessarily have to be analyzed. This can, however, ensue nevertheless.

In this context, the image analyzer 4 furthermore detects that the patient P must be situated on his or her side because, for example, the eye socket 8 or the nose 9 can also be detected in the image as anatomical markers insofar as they are visible therein, which does not necessarily have to be the case because the sagittal section does not necessarily have to be implemented at this height (level). Insofar as these structures are already detectable in the localizer image defined with regard to the x-axis and z-axis, using this exposure it can already be established that the patient P lies on his or her side looking to the left (relative to the insertion direction).

Insofar as the additionally sought anatomical marker "eye socket" or "nose" (which are, as stated, not absolutely necessary for position analysis in this case) cannot be detected in the sagittal image, the transversal localizer $A_{trans}$ (which is likewise shown in FIG. 4) is used. Using this binarized image, the eye socket 8 can now be detected as an asymmetric anatomical marker and the left-side position can be detected.

FIG. 5 shows a sagittal localizer exposure $A_{sag}$ in which both feet 10 of the patient are shown. In this binarized representation, the image analyzer 4 determines (for example via an edge detection algorithm) the black-white border line curve and detects both feet 10 without any doubts. Using the border line curve it is also possible to detect the chest-side or back-side positioning of the patient. In the shown example, the toes 11 point towards one another, which is typically the case when the patient lies on his or her stomach since then the toes are tilted towards one another. This means that the orientation is defined from the triangular shape in the foot region.

If it results from the sagittal exposure that the patient is lying on his or her side but the feet are nevertheless unambiguously detected (which can be determined without further measures from the typical foot shape), here the side orientation is also determined from the alignment of the feet or the direction of the toes (which then point to the right or to the left in the sagittal section).

Primarily in magnetic resonance devices with an open structural shape it is possible to centrally introduce the patient into the device as a consequence of the two-dimensional table displacement capability. An identification using the head or foot contour is then not possible. This means that only the torso, without specific anatomical head or foot markers, is shown in the respective localizer exposures.

In this case, using a sagittal localizer image $A_{sag}$ it is initially determined whether the patient is inserted into the scanner with the head, the feet, the legs or the torso.

In the sagittal image, FIG. 6 shows only a section of the torso 12 of the patient without any kind of anatomical markers that, for example, can be unambiguously associated with the hip region or the shoulder region. Only the spinal column 13 with some vertebrae is shown. The image analyzer 4 is now able to detect (using the vertebrae slice shape shown in the binarized sagittal section) whether the patient was inserted head-first or feet-first. The vertebrae in the sagittal section show a corresponding shape that then allows an unambiguous, directional association.

Using the transversal section image $A_{trans}$, the image analyzer 4 now determines whether the patient P lies on his or her back, his chest or side. Here the vertebrae are clearly situated in the lower region relative to the body outline 15; the patient is consequently lying on his or her back. Here an unambiguous position detection can therewith also be effected exclusively using the fast localizer exposures, preferably in binarized form, which position determination is then automatically entered into the registration (if applicable after acknowledgement by the operating personnel).

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for automatically determining a supported position of a patient in a magnetic resonance apparatus, comprising the steps of:
   prior to obtaining a medically diagnostic magnetic resonance image of a patient with the entirety of the patient in a predetermined diagnostic image overall orientation relative to a magnetic resonance apparatus, at a time selected from the group consisting of during insertion of a patient into the magnetic resonance apparatus and after insertion of a patient into the magnetic resonance apparatus, acquiring three non-medically-diagnostic magnetic resonance orthogonal localizer exposures of the patient;
   automatically electronically analyzing said three orthogonal localizer exposures to identify at least one anatomical marker that has a location in at least one of said three orthogonal localizer exposures that is determinative of an overall orientation of the entirety the patient in the magnetic resonance apparatus; and
   from said at least one anatomical marker, automatically identifying said overall orientation of the entirety of the patient relative to the magnetic resonance apparatus to insure conformity with said predetermined diagnostic image overall orientation of the subject.

2. A method as claimed in claim 1 comprising, before automatically electronically analyzing said three orthogonal localizer exposures, binarizing each of said three orthogonal localizer exposures to produce three binarized orthogonal localizer exposures, and automatically electronically analyzing said three orthogonal binarized localizer exposures.

3. A method as claimed in claim 2 wherein the step of binarizing said three orthogonal localizer exposures comprises binarizing said three orthogonal localizer exposures using grey scale value windowing parameters selected from the group consisting of fixed, predetermined grey scale value windowing parameters and user-adjustable grey scale value windowing parameters.

4. A method as claimed in claim 1 comprising automatically displaying the determined overall position of the entirety patient in the medical apparatus at a monitor, and requiring entry of an acknowledgement by an operator into the magnetic resonance apparatus before acquiring said magnetic resonance diagnostic image of the patient.

5. A magnetic resonance apparatus comprising:
   a magnetic resonance scanner configured to receive a patient therein;
   a control unit that operates said magnetic resonance scanner to obtain a medically diagnostic magnetic resonance image of the patient with the entirety of the patient in a predetermined diagnostic image overall orientation relative to the magnetic resonance scanner;
   prior to obtaining said medically diagnostic image, said control unit operating said magnetic resonance scanner to obtain three non-diagnostic magnetic resonance orthogonal localizer exposures of the patient in the magnetic resonance scanner; and
   an image analyzer supplied with said three orthogonal localizer exposures that automatically electronically analyzes said three orthogonal localizer exposures to identify at least one anatomical marker in at least one of said three orthogonal localizer exposures that is determinative of an overall position of the entirety of the patient in said scanner, and said image analyzer automatically determining said overall orientation of the patient relative to the magnetic resonance scanner from said at least one anatomical marker to insure conformity with said predetermined diagnostic image overall orientation of the patient.

6. A magnetic resonance apparatus as claimed in claim 5 wherein said image analyzer binarizes said three orthogonal localizer exposures before automatically electronically analyzing said three orthogonal localizer exposures.

7. A magnetic resonance apparatus as claimed in claim 6 wherein said image analyzer automatically binarizes said three orthogonal localizer exposures using fixed, predetermined grey scale value windowing parameters.

8. A magnetic resonance apparatus as claimed in claim 6 comprising an input unit allowing entry of inputs by an operator, and wherein said image analyzer binarizes said three orthogonal localizer exposures using grey scale value windowing parameters entered as an input by an operator via said input unit.

9. A magnetic resonance apparatus as claimed in claim 5 comprising an input unit allowing entry of inputs by an operator, and a display monitor, and wherein said image analyzer automatically causes the determined overall position of the entirety of the patient in the magnetic resonance scanner to be presented at said display monitor, and requires entry of an acknowledgement by an operator via said input unit before acquiring said diagnostic magnetic resonance image of the patient.

* * * * *